United States Patent
Raaheim et al.

(10) Patent No.: US 10,927,008 B2
(45) Date of Patent: Feb. 23, 2021

(54) METHOD AND DEVICE FOR UPGRADING OF BIOGAS AND HYDROGEN PRODUCTION FROM ANAEROBIC FERMENTATION OF BIOLOGICAL MATERIAL

(71) Applicant: ZEG Power AS, Kjeller (NO)

(72) Inventors: Arne Raaheim, Maura (NO); Julien Meyer, Oslo (NO); Björg Andresen, Oslo (NO); Nicola Di Giulio, Oslo (NO); Öystein Ulleberg, Oslo (NO)

(73) Assignee: ZEG Power AS, Kjeller (NO)

( * ) Notice: Subject to any disclaimer, the term of this patent is extended or adjusted under 35 U.S.C. 154(b) by 0 days.

(21) Appl. No.: 16/317,582

(22) PCT Filed: Jul. 7, 2017

(86) PCT No.: PCT/NO2017/050185
§ 371 (c)(1),
(2) Date: Jan. 14, 2019

(87) PCT Pub. No.: WO2018/012983
PCT Pub. Date: Jan. 18, 2018

(65) Prior Publication Data
US 2019/0241434 A1    Aug. 8, 2019

(30) Foreign Application Priority Data
Jul. 14, 2016    (NO) .................................... 20161174

(51) Int. Cl.
*C01B 3/34* (2006.01)
*C12P 5/02* (2006.01)
*C12P 3/00* (2006.01)

(52) U.S. Cl.
CPC ............... *C01B 3/344* (2013.01); *C12P 3/00* (2013.01); *C12P 5/023* (2013.01);
(Continued)

(58) Field of Classification Search
CPC .. C01B 3/344; C01B 3/34; C01B 3/56; C01B 2203/0233; C01B 2203/0238;
(Continued)

(56) References Cited

U.S. PATENT DOCUMENTS 6,790,430 B1 *   9/2004   Lackner .................... C01B 3/12
                                                                 423/648.1
2005/0229489 A1   10/2005   Bavarian et al.
(Continued)

FOREIGN PATENT DOCUMENTS

| | | |
|---|---|---|
| CN | 105084312 A | 11/2015 |
| EP | 1218290 B1 | 12/2004 |
| WO | 2014200357 A1 | 12/2014 |

OTHER PUBLICATIONS

International Search Report and Written Opinion dated Sep. 5, 2017 for International Patent Application No. PCT/NO2017/050185.

*Primary Examiner* — Nam X Nguyen
*Assistant Examiner* — Julia L. Wun
(74) *Attorney, Agent, or Firm* — Alix, Yale & Ristas, LLP

(57) ABSTRACT

Method and device for biogas upgrading and hydrogen production from anaerobic fermentation of biological material under production of energy rich gases selected among methane and hydrogen or a combination thereof. The method comprises addition of hydrogen gas to a fermentation step to enhance the methane: $CO_2$ ratio in the raw biogas produced. At least part of the raw biogas is subjected to a step of sorption enhanced reforming without prior separation of $CO_2$, using CaO as an absorbent to capture $CO_2$ from the raw biogas as well as $CO_2$ released in the reforming reaction. CaO is regenerated in an endothermic reaction using heat at least partially provided, directly or indirectly, by the bio-gas
(Continued)

to be upgraded, thereby producing substantially pure hydrogen and substantially pure $CO_2$.

20 Claims, 2 Drawing Sheets

(52) U.S. Cl.
CPC ........... *C01B 2203/0233* (2013.01); *C01B 2203/0238* (2013.01); *C01B 2203/043* (2013.01); *C01B 2203/0475* (2013.01); *C01B 2203/066* (2013.01); *C01B 2203/127* (2013.01); *C01B 2203/86* (2013.01); *Y02E 50/30* (2013.01); *Y02P 30/00* (2015.11)

(58) Field of Classification Search
CPC ...... C01B 2203/043; C01B 2203/0475; C01B 2203/066; C01B 2203/127; C01B 2203/86; C01B 2203/1258; C01B 2203/1241; C01B 2203/042; C01B 2203/04; C12P 3/00; C12P 5/023; Y02E 50/343; Y02P 30/30
USPC .............................. 210/603, 175, 180, 188
See application file for complete search history.

(56) References Cited

U.S. PATENT DOCUMENTS

| | | |
|---|---|---|
| 2007/0298478 A1 | 12/2007 | Offerman et al. |
| 2013/0011326 A1 | 1/2013 | Grover |
| 2013/0017460 A1* | 1/2013 | Keefer ............... B01D 53/047 429/419 |
| 2014/0342426 A1* | 11/2014 | Angelidaki ........... C12M 21/04 435/167 |
| 2015/0284247 A1 | 10/2015 | Lee et al. |

\* cited by examiner

METHOD AND DEVICE FOR UPGRADING OF BIOGAS AND HYDROGEN PRODUCTION FROM ANAEROBIC FERMENTATION OF BIOLOGICAL MATERIAL

BACKGROUND

The disclosure concerns a method for anaerobic fermentation of biological material under production of energy rich gases selected among methane and hydrogen.

Biogas can be produced by anaerobic digestion (AD) or fermentation of biodegradable materials, such as manure, wastewater and sewage sludge, municipal waste, green waste, plant material, and crops. Biogas consists mainly of methane ($CH_4$) and carbon dioxide ($CO_2$), and small amounts of hydrogen sulphide ($H_2S$), moisture, and siloxanes.

If the anaerobically produced biogas is to be used as a transportation fuel (vehicle grade), it first has to be upgraded to remove impurities and increase its calorific value (heating value). This upgrading step includes drying, desulfurization, and $CO_2$-removal. The $CO_2$-separation is normally carried out by water scrubbing, physical or chemical absorption using organic solvents, pressure swing adsorption, or by permeation using membranes, depending on the location and size of the system.

In a presentation made at Group Exhibit 2015 Hydrogen Fuel Cells Batteries, Apr. 14, 2015), as also documented in Energia Procedia 63 (2014) 279-285, published by Elsevier Ltd., a plant for so-called bio-ZEG methane was presented and discussed, including the use of solid oxide fuel cells and use of CaO as a $CO_2$ scavenger. There was, however, no mention of using raw $CO_2$ containing biogas as a source feed for such a process.

US 2015 0284247 A1 teaches an apparatus for producing high-purity gas which includes a column configured for sorption-enhanced reaction (SE-SMR) for removing a by-product through a catalyst reaction. The column is divided into a plurality of sections, the sections having decreasing proportions of catalyst and increasing proportions of an absorbent.

US 2013 011326 A1 and DE 19 946 381 A1 are other publications in this technical field.

However, one of the main drawbacks and challenges with biogas is the requirement for upgrading to bio-methane, with a quality for use as fuel for (bio) gas vehicles, or as a source for hydrogen fuel cell electric vehicles (FCEVs). Biogas from food waste (or other sources such as manure and wastewater) treatment facilities typically consist of 55-65% $CH_4$ and 35-45% $CO_2$. Upgrading ($CO_2$ removal) consumes energy and adds significant costs to the overall system (Luo and Angelidaki, 2012). Hence, there is a need to find new, more efficient, and less costly methods for upgrading anaerobically produced biogas for example used directly as fuel in vehicles, and as a source for hydrogen production used in hydrogen fuel cell electric vehicles.

There is still, however, a need for further improvements in this area to make fuel produced by digestion of organic waste competitive as vehicle fuel.

This can to some extent be achieved by reduction of the $CO_2$ content and enhancement of the methane content, by adding hydrogen to the anaerobic digestion (AD) process, thereby increasing the methane content to about 80%

SUMMARY OF THE INVENTION

Provided herein is a new and cost-efficient process and device that allow production of vehicle grade fuels based on anaerobic digestion of wet organic substrates, with $CO_2$ capture or no negative climate consequence.

By "raw biogas" as discussed herein is understood a biogas from which Sulfur have been removed but in which the content of $CO_2$ is as originated from the anaerobic digester reactor, contrary to upgraded biogas which is essentially pure methane.

Addition of $H_2$ to the digestion process increases the ratio between bio-methane and $CO_2$, with $CO_2$ content potentially lower than 20%.

The inventive embodiments provide for the conversion of the raw biogas with enhanced methane: $CO_2$ ratio directly in a sorption enhanced reforming (SER) process without prior separation of $CO_2$. This is achieved by dimensioning the reformer 70 to capture both $CO_2$ from the initial desulfurized raw biogas ($CH_4$+$CO_2$) and the $CO_2$ formed in the reforming step (SE-SMR process).

Ca-looping has, to our knowledge, not been suggested as a method for $CO_2$ removal in relation to production of hydrogen from raw biogas or gases with considerable amounts of initial $CO_2$ in addition to methane.

The total SER-process with desulfurized raw biogas as feed gas is illustrated in the chemical reaction (not balanced) given below;

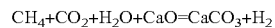

$$CH_4+CO_2+H_2O+CaO=CaCO_3+H_2$$

Two alternative embodiments are illustrated below, namely (1) Biological conversion of $CO_2$ to $CH_4$ by the addition of $H_2$ from an SER-process in an AD reactor and (2) Direct conversion of desulfurized raw biogas ($CH_4$+$CO_2$) to hydrogen in a SER reactor.

As illustrated and exemplified below, one embodiment provides a combined system for production of vehicle grade biomethane, and vehicle grade hydrogen, with the option of total $CO_2$ capture, from anaerobic digestion of organic waste.

Cost efficiency and sustainability are keyword and common denominators for the overall process.

BRIEF DESCRIPTION OF THE DRAWINGS

Different embodiments of the invention are illustrated below with reference to the enclosed drawings, where.

DETAILED DESCRIPTION

Figure 1:
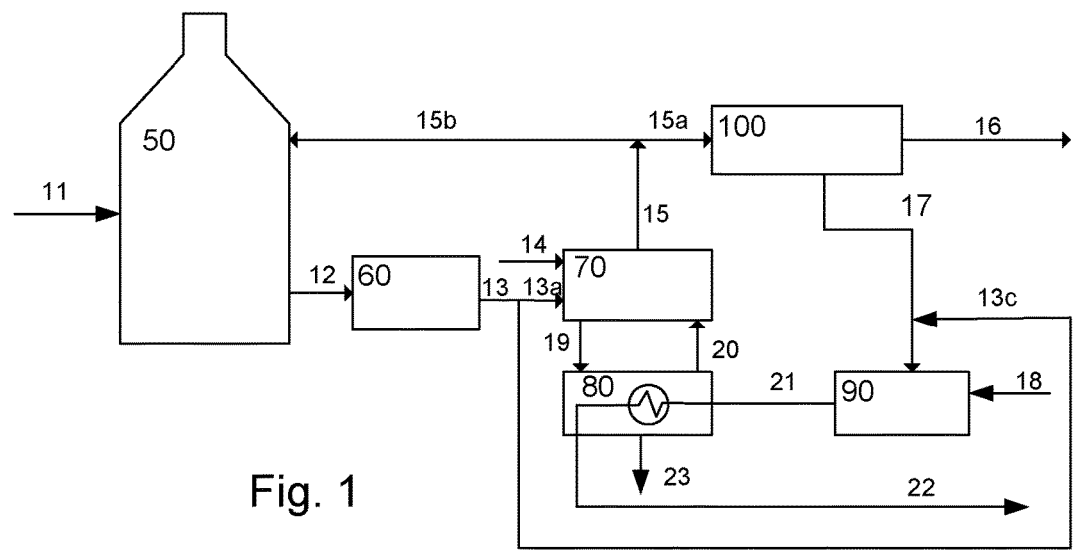
FIG. 1 is a schematic view of a first embodiment of the disclosure, in which vehicle grade hydrogen is produced from anaerobic fermentation of biological material in a cost-efficient and sustainable manner.

Attention is drawn to FIG. 1. An anaerobic digester 50 for biogas production is charged with a charge material 11 based on sewage sludge, domestic organic waste, animal or agricultural waste. The produced raw biogas 12 is desulfurized 60, and the desulfurized, still raw biogas 13 ($CH_4$+initial $CO_2$) is charged to a reformer 70 together with water 14 in the form of steam for a sorption enhanced reforming (SER) process. A substantially pure hydrogen 15 gas leaves the reformer unit. In the reformer unit, one part 15b of which typically being returned to the digester 50 to enhance the methane yield while another and typically larger part 15a is subjected to purification in a hydrogen-purifier 100. The hydrogen purification may typically be performed as a pressure swing adsorption process. The purified hydrogen 16 leaving the purifier is of vehicle grade.

While the step of desulfurization 60 is a step commonly used in such processes and not inventive as such, it is a step which for practical chemical purposes will rarely or never be omitted.

The process of reforming and $CO_2$ capture in the reformer 70 involves a reaction between fuel ($CH_4$), water (steam), $CO_2$ (both from the original biogas and from the SER process) and CaO as a $CO_2$ absorber, a process in which CaO is converted to $CaCO_3$ in an exothermic reaction known per se.

The off-gas 17 from the hydrogen purification unit 100 is mixed with raw biogas 13c, which may be a partial flow of biogas flow 13, and charged to a burner 90 for production of the necessary heat (850 to 900° C.) for regeneration of $CaCO_3$ to CaO in a CaO regenerator 80, in an endothermic process. The $CO_2$ (100%) flow 23 produced in the reformer 70 and released in regenerator 80, may be used or stored (sequestration). The burner 90 is also charged with an oxygen containing gas 18, typically air.

The $CO_2$ in the exhaust from the burner 90 would have no climatic consequence since the fuel source is of biogenic origin. In addition, the $CO_2$ flow captured as flow 23 has a "negative" $CO_2$ climate impact, if this flow of $CO_2$ is stored or used.

Flow 19 is a flow from the reformer 70 to the regenerator 80 of solid $CaCO_3$, resulting from CaO having absorbed $CO_2$, while flow 20 is a flow of solid CaO, converted back from $CaCO_3$, from the regenerator 80 back to the reformer 70. This Ca-looping process is well known as such, but not in the context here presented.

Figure 2:
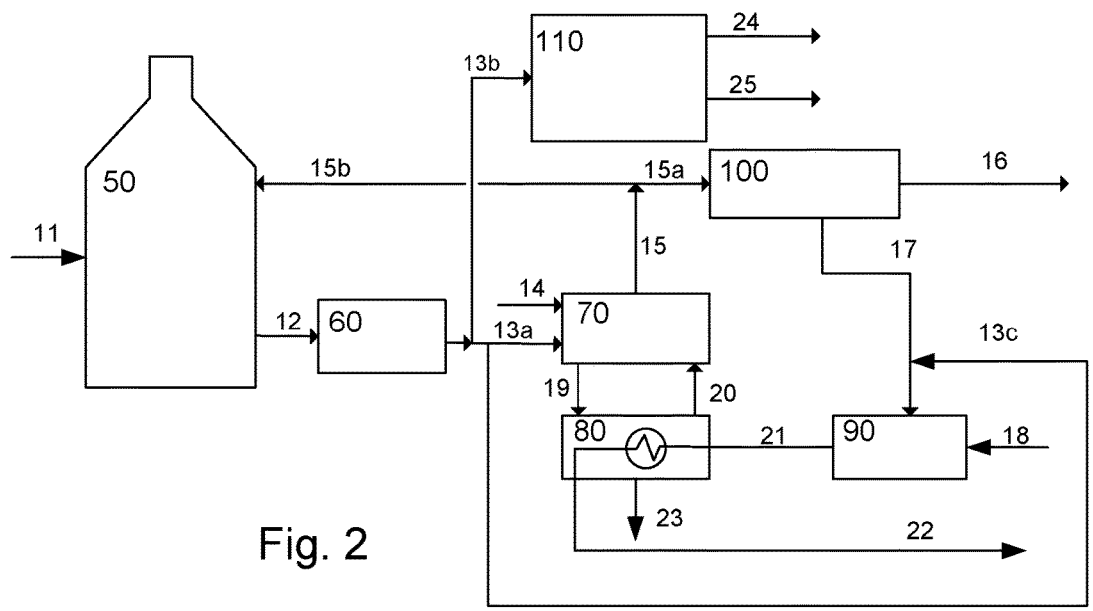
FIG. 2 is a schematic view of another embodiment of the disclosure, in which vehicle grade hydrogen and vehicle grade biomethane is produced from anaerobic fermentation of biological material in a cost-efficient and sustainable manner.

Attention is now directed to FIG. 2. Most of the components and flows of FIG. 2 are the same as the ones in FIG. 1 and are numbered equally. The process according to FIG. 2, however, has the additional ability of producing vehicle grade biogas. A first part 13a of the desulfurized biogas 13 is charged to the reformer 70 like in FIG. 1 and treated accordingly. A second part of the biogas 13b from the desulfurization unit 60 is charged to a $CO_2$ separation unit 110. The $CO_2$-separation is normally carried out by water scrubbing, physical or chemical absorption using organic solvents, pressure swing adsorption, or by permeation using membranes, depending on the location and size of the system. The bio methane 24 discharged from $CO_2$ separation unit 110 may be said to be of natural gas quality or of vehicle grade and hence used for such purposes.

The $CO_2$ 25 released from the $CO_2$ separation unit 110 may be stored or used, if the method applied makes this economically feasible. This is however usually not the case. Regardless of the method used, the biogenic origin of the fuel source would result in no climatic consequence. The purity of the $CO_2$ 25 released from the $CO_2$ separation unit 110 depends on the type and nature of this unit.

Figure 3:
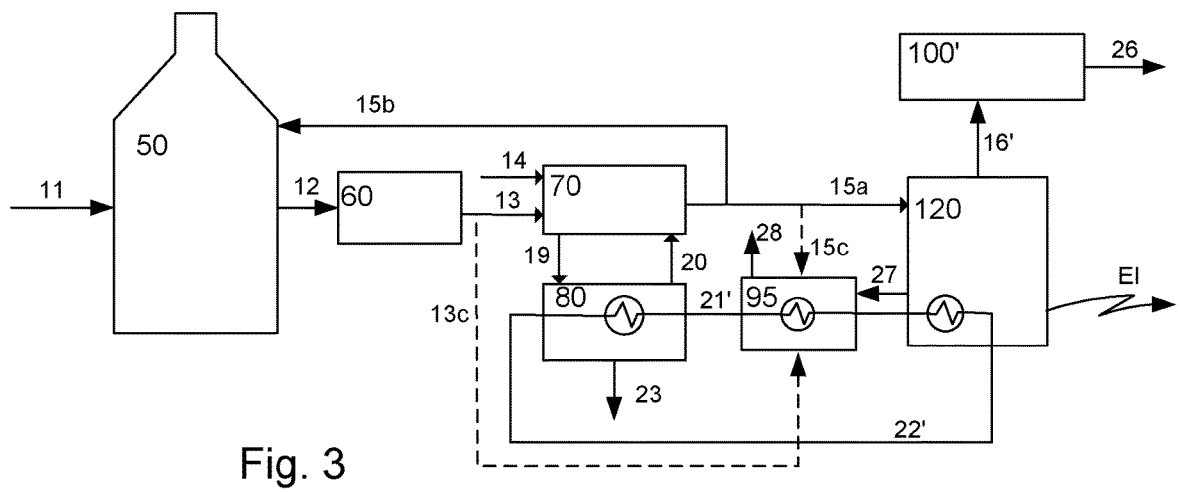
FIG. 3 is a schematic view of a third embodiment of the disclosure, in which vehicle grade hydrogen is produced from anaerobic fermentation of biological material in a cost-efficient and sustainable manner, while also producing electricity.

Attention is now directed to FIG. 3. Most of the components of FIG. 3 are the same as the ones in FIG. 1 and are equally numbered. The process according to FIG. 3, however, has the additional ability of producing electricity and high temperature heat due to the presence of a solid oxide fuel cell (SOFC) integrated in the process and equipment. Thus, the substantially pure hydrogen discharged from the reformer, is typically divided into three substreams, namely substream 15a which is charged to the SOFC, substream 15b which is recycled to the digester 50 (like in FIGS. 1 and 2) and substream 15c which, when present, is used as a fuel for a heater 95.

The hydrogen substream 15a is partially used to produce electricity in the SOFC while another part of the hydrogen flow 16' leaves the SOFC for further upgrading in a hydrogen purifier 100' which may or may not be similar to the unit 100 shown in FIGS. 1 and 2 to obtain vehicle grade hydrogen 26. The electricity may be used internally or externally or both.

The high temperature exhaust gas of the SOFC is used to heat the regenerator 80, but may typically need some assistance since the temperature needed in the regenerator 80 is 850 to 900° C. This temperature may be reached (without any assistance) if ceramic interconnects are used in the SOFC system.

In practice, however, the temperature of the exhaust gas (830° C., Megel et. al 2013) is too low to effectively provide a temperature in the regenerator at which the $CaCO_3$ is converted to CaO for further use. A dedicated system, to elevate the temperature of the exhaust gas in a temperature increasing cell/heating device, would thus be necessary.

The heat integration between the SOFC 120 and the Regenerator 80, via the heater 95, is in FIG. 3 provided by a closed heat loop 21', 22', however other options are possible.

The heat transfers medium of the heat loop 21', 22' in FIG. 3, can be different gases, such as for example; Hydrogen, $CO_2$, air, helium, water vapor, different gas mixtures or fluids such as; mineral oils, hydrocarbons and different types of molten salts. The heat of the heat loop in FIG. 3, leaving the SOFC system, is typically about 830° C. The heat of this heat loop is enhanced in the heater 95 to at least 850° C., more preferable at least 950° C. and most preferred at least 1000° C., in order to meet the temperature regeneration requirement in the regenerator 80 where $CaCO_3$ is converted to CaO while releasing $CO_2$. While the heater 95 may be heated in different ways, one convenient way is the use of a partial flow of hydrogen 15c from the reformer. Another option for fuel to 95 would be raw biogas 13c. Whether the fuel for the heater has the form of raw biogas 13c according to FIG. 1, 2, or 4 or hydrogen 15c according to FIG. 3, the heat delivered by the burner 90 or by the heater 95 is at least partially provided, directly or indirectly, by the desulfurized raw bio-gas to be upgraded. The SOFC exhaust air 27 provides the oxygen for the heating process in 95. The $CO_2$ in the exhaust outlet 28 from the heating device would be climate neutral because of the biogenic origin of the fuel used. If required, additional air (not shown) may be supplied to the heater 95.

Figure 4:
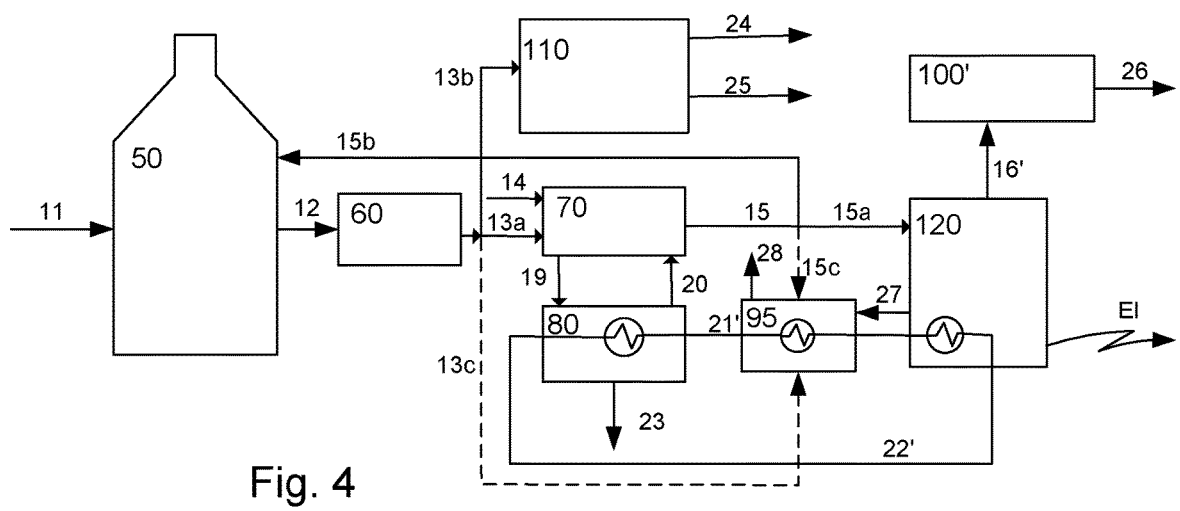
FIG. 4 is a schematic view of a fourth embodiment of the disclosure, in which vehicle grade hydrogen and vehicle grade biomethane is produced from anaerobic fermentation of biological material in a cost-efficient and sustainable manner, while also producing electricity.

Attention is now directed to FIG. 4. Most of the components in FIG. 4 are the same as in FIG. 3. The process of FIG. 4, however, has the additional ability of allowing production of vehicle grade biogas, in a manner similar to the difference between FIG. 1 and FIG. 2.

Thus, according to FIG. 4, the flow of desulfurized biogas 13 is split into a first flow 13a which is charged to the reformer 70 while the other flow 13b is charged to a $CO_2$ separation unit 110 to be separated into vehicle grade biomethane 24 and $CO_2$ 25. The treatment of the first flow 13a is as described above in relation to FIG. 1, while the other flow 13b is subjected to a treatment as generally described in relation to FIG. 2.

With regard to the SOFC and the processes involved therein, there is no difference between the embodiments of FIGS. 3 and 4. The same is to be said about the closed loop heat exchange 21', 22' including the use of the heater 95.

It is to be understood that the processes according to FIGS. 2 and 4 allows a split of the desulfurized raw biogas into a first flow 13a and a second flow 13b, covering a ratio between the two from 5:95 to 100:0. Thus, if demand is high for vehicle grade biomethane and low for vehicle grade hydrogen and electricity, the flow 13a would be reduced so as to basically just cover the need for hydrogen in the digester. On the other hand, if the demand for vehicle grade biomethane is low, the flow 13b could basically be cut off, rendering the embodiment of FIG. 2 temporarily identical to the embodiment of FIG. 1 and/or rendering the embodiment of FIG. 4 temporarily identical to the embodiment of FIG. 3.

The general concept disclosed herein is a method for the manufacture of vehicle grade fuels from biological materials in a cost-efficient and sustainable manner, involving a minimum of steps. There is a versatility in the method in the sense that vehicle grade biomethane and vehicle grade hydrogen may be produced at a flexible mutual ratio, as well as flexible amounts of electricity.

While not representing the core of the inventive concepts disclosed herein, a step of desulfurization 60 is typically conducted upstream of the step of sorption enhanced reforming 70.

As explained in relation to the drawings, a partial flow of desulfurized biogas 13 is according some embodiments subjected to treatment in a $CO_2$ separation unit 110 thereby providing one discharge flow of vehicle grade biomethane 24 and one discharge flow 25 containing $CO_2$.

The $CO_2$ separation unit 110 is typically one using a principle for separation selected among water scrubbing, physical or chemical absorption using organic solvents, pressure swing adsorption, and permeation using membranes.

According to at least some embodiments the heat required for regenerating CaO is provided by burning a gas containing a partial flow of desulfurized biogas. In some embodiments heat for regeneration of CaO may also be provided in part from a solid oxide fuel cell 120 charged with hydrogen 15a from the sorption enhanced reforming step 70. Additional heat may in case be provided by a heater 95 charged with hydrogen 15c discharged from the sorption enhanced reforming step 70. In other embodiments the fuel cell 120 may be charged with raw biogas or a combination of hydrogen and raw biogas.

In some embodiments a heat medium 21', 22' is circulated in a closed loop between at least the solid oxide fuel cell 120, the heater 95 and the regenerator 80. The addition of hydrogen to the digestion process may be arranged at least in part as a recycle hydrogen flow 15b from the reforming step 70.

In a number of embodiments the raw biogas to be upgraded is produced in a digestion process based on digestion of a raw material selected among one or more of sewage, sludge, municipal waste, domestic waste, animal waste, and agricultural waste.

LIST OF REFERENCES 11 feed to digester 50
12 biogas from digester 50
13 desulfurized biogas to reformer 70
13a partial flow desulfurized biogas to reformer 70
13b desulfurized biogas to $CO_2$ separator 110
13c raw, desulfurized biogas to heater 95/burner 90
14 water to reformer 70
15 substantially pure hydrogen from reformer 70
15a partial flow hydrogen to reformer 70
15b recycle partial flow of hydrogen to digester 50
15c partial hydrogen flow to heater 95
16 vehicle grade hydrogen from hydrogen purifier 100
16' Subst pure hydrogen from SOFC 120
17 off gas from hydrogen purifier 100
18 air inlet to burner 90
19 $CaCO_3$ from reformer 70 to regenerator 80
20 CaO from regenerator 80 to reformer 70
21 hot gas from burner 90 to regenerator 80
21' hot gas from heater 95 to regenerator 80
22 off gas from regenerator 80
22' off gas from regenerator to SOFC 120 in closed loop
23 $CO_2$ from regenerator 80
24 vehicle grade bio-gas from $CO_2$ separator 110
25 $CO_2$ from $CO_2$ separator 110
26 Vehicle grade hydrogen from 100'
27 Exhaust from SOFC 120
28 Exhaust from heater 95
50 digester
60 desulfurizer
70 reformer
80 regenerator
90 burner
95 heater
100 hydrogen purifier
100' hydrogen purifier
110 $CO_2$ separator
120 solid oxide fuel cell

The invention claimed is:

1. A method for upgrading biogas from anaerobic fermentation of biological material under production of energy rich gases selected from one or more of methane (24) and hydrogen (16, 26), comprising
   in a fermentation step (50) that produces raw biogas (12), adding hydrogen gas to increase a ratio of methane: $CO_2$ in the raw biogas (12) produced;
   desulfurizing the raw biogas;
   subjecting at least a portion of the desulfurized raw biogas to sorption enhanced reforming (70) without prior separation of $CO_2$,
   capturing $CO_2$ from the raw biogas and $CO_2$ released in the reforming reaction using CaO as an absorbent,
   regenerating CaO in an endothermic reaction (80) using heat at least partially provided, directly or indirectly, by the biogas to be upgraded, thereby producing substantially pure hydrogen (15) and substantially pure $CO_2$ (23).

2. The method as claimed in claim 1, wherein the desulfurizing comprises desulfurization upstream of the step of sorption enhanced reforming (70).

3. The method as claimed in claim 1, comprising treating a partial flow of desulfurized raw biogas (13) in a $CO_2$ separation unit (110), thereby providing one discharge flow of vehicle grade biomethane (24) and one discharge flow (25) containing $CO_2$.

4. The method as claimed in claim 3, wherein the $CO_2$ separation unit (110) uses a principle for separation selected from the group consisting of water scrubbing, physical or chemical absorption using organic solvents, pressure swing adsorption, and permeation using membranes.

5. The method as claimed in claim 1, comprising further purifying (100) the substantially pure $H_2$ (15) to produce vehicle grade $H_2$ (16).

6. The method as claimed in claim 1, wherein heat for regenerating CaO is provided by burning a gas containing a partial flow of desulfurized raw biogas (13c).

7. The method as claimed in claim 3, wherein heat for regenerating CaO is provided by burning a gas containing a partial flow of desulfurized raw biogas (13c).

8. The method as claimed in claim 1, wherein heat for regeneration of CaO is provided in part from one or more of the group consisting of a solid oxide fuel cell (120) charged by hydrogen (15a) from the sorption enhanced reforming step (70) and by desulfurized raw biogas (13c).

9. The method of claim 3, wherein heat for regeneration of CaO is provided in part from one or more of the group consisting of a solid oxide fuel cell (120) charged by hydrogen (15a) from the sorption enhanced reforming step (70) and by desulfurized raw biogas (13c).

10. The method as claimed in claim 8, wherein additional heat for regeneration of CaO is provided by a heater (95) charged with hydrogen (15c) discharged from the sorption enhanced reforming step (70).

11. The method as claimed in claim 8, wherein a heat medium (21', 22') is circulated in a closed loop between at least the solid oxide fuel cell (120), a heater (95) and a regenerator (80).

12. The method as claimed in claim 10, wherein a heat medium (21', 22') is circulated in a closed loop between at least the solid oxide fuel cell (120), the heater (95) and a regenerator (80).

13. The method as claimed in claim 1, wherein the raw biogas to be upgraded is produced in the fermentation step (50) based on digestion of a raw material selected from one or more of the group consisting of sewage, sludge, municipal waste, domestic waste, animal waste, and agricultural waste.

14. The method as claimed in claim 3, wherein the raw biogas to be upgraded is produced in the fermentation step (50) based on digestion of a raw material selected from one or more of the group consisting of sewage, sludge, municipal waste, domestic waste, animal waste, and agricultural waste.

15. The method as claimed in claim 6, wherein the raw biogas to be upgraded is produced in the fermentation step (50) based on digestion of a raw material selected from one or more of the group consisting of sewage, sludge, municipal waste, domestic waste, animal waste, and agricultural waste.

16. The method as claimed in claim 11, wherein the addition of hydrogen to the fermentation step is arranged at least in part as a recycle hydrogen flow (15b) from the reforming step (70).

17. A device for upgrading biogas from anaerobic fermentation of biological material under production of energy rich gases, selected from one or more of methane (24) and hydrogen (16), comprising:
   a digester (50),
   a device (60) for desulfurization,
   a reformer unit (70, 80),
   wherein the reformer unit (70, 80) is arranged downstream of the digester (50) and the device (60) for desulfurization, for reforming according to sorption enhanced reforming principle based on Ca-looping to provide a reforming which is inherently integrated with carbon capture and subsequent purification of the hydrogen with a hydrogen purification unit (100, 100').

18. The device as claimed in claim 17, comprising a solid oxide fuel cell (120) arranged to receive at least a portion of a gas discharged from the reformer unit, and a gas discharged from the solid oxide fuel cell to be purified in the hydrogen purification unit.

19. The device as claimed in claim 17, comprising a solid oxide fuel cell (120) arranged to receive at least part of a gas discharged from the reformer unit, wherein the solid oxide fuel cell is configured to be charged for production of electric energy and heat.

20. The device as claimed in claim 17, wherein part of a gas discharged from the device for desulfurization is charged to a $CO_2$ separation unit for separation into a vehicle grade biomethane (24) and pure $CO_2$ (25).

* * * * *